US008244654B1

(12) United States Patent
Hobgood et al.

(10) Patent No.: US 8,244,654 B1
(45) Date of Patent: Aug. 14, 2012

(54) END OF LIFE PREDICTIVE MODEL

(75) Inventors: Adam Hobgood, Smyrna, TN (US); G. Brent Hamar, Nashville, TN (US); Angela Dobbs, Smyrna, TN (US); Karen Hamlet, Clarksville, TN (US); Matthew McGinnis, Franklin, TN (US); Michael Montijo, Nashville, TN (US)

(73) Assignee: Healthways, Inc., Franklin, TN (US)

( * ) Notice: Subject to any disclaimer, the term of this patent is extended or adjusted under 35 U.S.C. 154(b) by 823 days.

(21) Appl. No.: 12/340,491

(22) Filed: Dec. 19, 2008

Related U.S. Application Data

(63) Continuation of application No. 12/023,983, filed on Jan. 31, 2008, now abandoned.

(60) Provisional application No. 60/981,798, filed on Oct. 22, 2007.

(51) Int. Cl.
G06E 1/00 (2006.01)
G06E 3/00 (2006.01)
G06F 15/18 (2006.01)
G06G 7/00 (2006.01)

(52) U.S. Cl. ............ 706/21; 706/15; 706/20; 706/45; 706/62; 702/19; 600/300; 600/301

(58) Field of Classification Search .................. None
See application file for complete search history.

(56) References Cited

U.S. PATENT DOCUMENTS

| | | | | |
|---|---|---|---|---|
| 5,769,074 | A * | 6/1998 | Barnhill et al. | 600/300 |
| 6,059,724 | A * | 5/2000 | Campell et al. | 600/300 |
| 6,306,087 | B1 * | 10/2001 | Barnhill et al. | 600/300 |
| 7,392,201 | B1 * | 6/2008 | Binns et al. | 705/4 |
| 7,461,048 | B2 * | 12/2008 | Teverovskiy et al. | 706/62 |
| 7,467,119 | B2 * | 12/2008 | Saidi et al. | 706/21 |
| 2003/0172043 | A1 * | 9/2003 | Guyon et al. | 706/48 |
| 2005/0203777 | A1 * | 9/2005 | Rosenfeld et al. | 705/3 |
| 2006/0036619 | A1 * | 2/2006 | Fuerst et al. | 707/100 |
| 2006/0195269 | A1 * | 8/2006 | Yeatman et al. | 702/20 |
| 2006/0248031 | A1 * | 11/2006 | Kates et al. | 706/25 |
| 2007/0021987 | A1 * | 1/2007 | Binns et al. | 705/4 |
| 2007/0185656 | A1 * | 8/2007 | Schadt | 702/19 |
| 2008/0033658 | A1 * | 2/2008 | Dalton et al. | 702/19 |
| 2008/0086325 | A1 * | 4/2008 | James | 705/2 |

OTHER PUBLICATIONS

Canadian Institute of Actuaries, CIA Perspectives: The High Cost of Dying, Document No. 202062, 2002, 2 pages.

Cousins et al., An Introduction to Predictive Modeling for Disease Management Risk Stratification, Disease Management, Sep. 1, 2002, 5(3): 157-167.

Crawford et al., Comparative Effectiveness of Total Population versus Disease-Specific Neural Network Models in Predicting Medical Costs, Disease Management, Oct. 1, 2005, 8(5): 277-287.

Huynh et al., Long-term Survival in Elderly Patients Hospitalized for Heart Failure, Arch Intern Med, Sep. 25, 2006, vol. 166: 1892-98.

(Continued)

*Primary Examiner* — Omar Fernandez Rivas

(74) *Attorney, Agent, or Firm* — Suiter Swantz pc llo

(57) ABSTRACT

A statistical processing system to predict end of life status in current patients of a given population. The processing system includes a server configured with programming instructions implementing a plurality of statistical models to predict a health status or outcome for the highest risk of death based on proprietary factors and the patient being administered no further therapeutic treatment.

56 Claims, 7 Drawing Sheets

OTHER PUBLICATIONS

Kudyba et al., Utilising neural network applications to enhance efficiency in the healthcare industry: predicting populations of future chronic illness, Int.J. Business Intelligence and Data Mining, vol. x, No. x, pp. 1-13, unknown date.

Kudyba et al., Utilising neural network applications to enhance efficiency in the healthcare industry: predicting populations of future chronic illness, Int.J. Business Intelligence and Data Mining, vol. 1, No. 4, pp. 371-383, 2006.

* cited by examiner

FIG. 4A

| Factor Name |
|---|
| SNF_CLAIM_CT |
| DIST_CHF_HOSP_VISIT_CLAIM_CT |
| DIST_SOMA_DIAGNOSIS_2_CT |
| MODEL_YEAR_END_MEMBER_AGE |
| PHYS_CHARGES_PAID_TOTAL_AMT |
| CHARGES_PAID_AMT_SL |
| DIST_CHF_ER_VISIT_CLAIM_CT |
| DIST_DIAB_HOS_VISIT_CLAIM_CT |
| DIST_DME_CODE_CT |
| HH_CHARGES_PAID_TOTAL_AMT |
| CHARGES_PAID_TOTAL_AMT |
| DIST_CHF_HOSP_VISIT_CLAIM_SL |
| DRG_TOTAL_PAYMENT_LOG |
| OUTPAT_CHARGES_PAID_AMT_SL |
| SNF_CHARGES_PAID_TOTAL_LOG |
| Data Field |
| CLAIM_ID |
| AHSI VISIT IND |
| AHSI_POS |
| DISC_DATE |
| DATE_OF_SERVICE_TO |
| ADM DATE |
| DATE OF SERVICE |
| ICD_CODE1-11 |
| DOB |
| CMS SPECIALTY |
| TOT_DOLS |
| CLAIM_LINE_TOTAL |
| HOP_CHF |
| DRG_TOTAL_PAYMENT_AMT |
| OP-DOLS |
| SNF_CHARGES_PAID_TOTAL_AMT |

FIG. 4

| FIG. 4A | FIG. 4B | FIG. 4C |

FIG. 4B

| Description |
|---|
| Count of Skilled Nursing Facility Claims |
| Count of District Hospital Visits CHF Diagnosis |
| Count of District Claims with Sealed Pain-Related Diagnoses |
| Member Age as of End of Year Used in Model |
| Total Amount Paid for Physician Claims |
| Change In Total Dollars from the First Half of the Year to Total Dollars from the Second Half of the Year |
| Count of District ER Visits with CHF Diagnosis |
| Count of District Hospital Visits with Diabetes Diagnosis |
| Count of Distinct Durable Medical Equipment Claims |
| Total Amount Paid for Home Health Claims |
| Total Amount Paid for All Claims |
| Change In Count of District Hospital Visits with CHF Diagnosis from the First Half of the Year to the Count from the Second Half of the Year |
| Natural Log of the Payment for Diagnosis Related Groups |
| Change In Outpatient Charges from the First Half of the Year to Outpatient Charges from the Second Half of the Year |
| Natural Log of Skilled Nursing Facility Charges |

| Description |
|---|
| ID to identify unique claim |
| Internal Indicator of type of visit-impatient, outpatient, ER, etc |
| Internal Indicator of place of service-hospital, office, etc |
| Discharge data |
| Data Indicating last date of service on claim |
| Admission date |
| Date Indicating first date of service on claim |
| ICD diagnosis codes in positions 1 through 11 |
| Date of birth |
| Provider specialty code as defined by CMS |
| Internal Indicator for total dollars |
| Total dollars on claim |
| Internal Indicator of count of CHF hospital visit claims |
| Total payment for Diagnosis Related Groups |
| Internal Indicator for total outpatient dollars |
| Total amount paid for skilled Nursing Facility claims |

FIG. 4C

| Rules |
|---|
| SNF=Skilled Nursing Facility. Similar to RX_CLAIM_CT but counting skilled nursing facility claims. |
| Count(District CLAIM_ID) where [AHSI_VISIT_IND in ('I',"X") OR AHSI_POS in ('21','31','32','33','35','54','61') OR nvl(DISC_DATE,DATE_OF_SERVICE_TO)-nvl(ADM_DATE,DATE_OF_SERVICE)>=1] AND [first 3 characters of ICD_CODE1-11'='425' OR ICD_CODE1-11 in ('39891','7245','7247',72479','7242','7243','7244','7865','78079','7807','30780,'30781','7840','30653','2512','78601','78791','7804','7820','78605','78606','78609','7851','V1582','V1581') |
| Count(District CLAIM_ID) where first 3 characters of ICD_CODE1-11 in ('346','V62','V69') OR first 4 characters of ICD_CODE1-11 in ('7890','7884','3074','7805','7195') OR ICD_CODE1-11 in ('30789','7245','7247',72479','7242','7243','7244','7865','78079','7807','30780','30781','7840','30653','2512','78601','78791','7804','7820','78605','78606','78609','7851','V1582','V1581') |
| floor( dtEndDate-dtModalDOB)/365.25 |
| Sum(CLAIM_LINE_TOTAL) where CMS_SPECIALTY in ('2','3','4','5','6','7','10','13','14','18','19','20','22','24','25','28','29','30','33','34','36','39','40','44','46','48','66','76','77','78','79','81','82','83','85','90','91','92','93','94','98','26','1','8','11','16','37','38','84') |
| TOT_DOLS from second half - TOT_DOLS from first half |
| Count(Distinct CLAIM_ID) where [AHSI_VISIT_IND in ('E','X') OR AHSI_POS in ('23')] AND [first 3 characters of ICD_CODE1-1='425' OR ICD_CODE1-11 in ('39891','40201','40211','40291','40401','40403','40411','40413','40491','40493','4280','4281','4'4289')] |
| Count(Distinct CLAIM_ID) where [AHSI_VISIT_IND in ('I','X') OR AHSI_POS ('21','31','32','33','35','54','61') OR nvl(DISC_DATE,DATE_OF_SERVICE_TO) - nvl(ADM_DATE,DATE_OF_SERVICE)>=1] AND [first 3 characters of ICD_CODE1-11='250' OR first 4 characters of ICD_CODE1-11 ='3620' ] |
| DME=Durable Medical Equipment. Similar to DIST_PROC_CODE_CT but counting DME codes. |
| HH=Home Health. Similar to RX_CHARGES_PAID_TOTAL_AMT but summing home health costs. |
| Sum(CLAIM_LINE_TOTAL) |
| HOSP_CHF from second half - HOSP_CHF from first half |
| DRG=Diagnosis Related Groups. This would be the natural log (LN function) of DRG_TOTAL_PAYMENT_AMT (since this is from a table and not an amount entered on a claim, there should be no values less than $1). |
| OP_DOLS from second half - OP_DOLS from first half |
| SNF=Skilled Nursing Facility. This would be the natural log (LN function) SNF_CHARGES_PAID_TOTAL_AMT. The exception would be values of SNF_CHARGES_PAID_TOTAL_AMT that are less than $1. Such values would have the log set to 0. |

END OF LIFE PREDICTIVE MODEL

CROSS-REFERENCE TO RELATED APPLICATIONS

This application is a continuation of U.S. application Ser. No. 12/023,983, filed Jan. 31, 2008, which claims the benefit of U.S. Provisional Application No. 60/981,798, filed Oct. 22, 2007, the disclosures of which are incorporated herein by reference in their entireties.

BACKGROUND OF THE INVENTION

1. Field of the Invention

The invention relates to methods and systems that provide computerized health care management, and more specifically, to a method and systems providing statistical assessment and prognostic information for individuals who are identified as being at the end of life within a predetermined period of time.

2. Description of the Related Art

The past decade of health services research has witnessed an explosion of prognostic models to help physicians understand the risks and benefits of proposed medical therapies and how to best treat patients in a given affliction subgroup. However, the application of such models to clinical practice has been limited by both their complexity and the lack of a practical mechanism for making them available at the time when medical decisions are made.

One goal of medical care is to make treatment recommendations to patients commensurate with their goals and values. To achieve this goal, one must describe the risks and benefits of a treatment that are relevant to given patient's situation. Models exist—currently these models remain largely academic and without a practical method or mechanism for being used in routine clinical care.

Computerized expert systems process information that usually corresponds to rules or procedures that are applied by human experts to solve similar problems. These systems do not utilize computerized predictive modeling to predict health events.

SUMMARY OF THE INVENTION

A system that combines the use of artificial intelligence to predict the end of life period in patient. A preferred embodiment discloses a system for identifying patients needing healthcare, comprising: a first module for preparation of patient data for input to statistical modeling submodules; a second module for evaluating outcome data of the statistical modeling submodules and establishing the predictive values meeting a predetermined criteria and applying the values to a first set of neural net models; and a third module configured to apply the results from the first set of neural net models to a second set of neural net models and generate a results set indicative of patients needing healthcare, wherein the patient data comprises data from a pre-determined population set. Patient data can be government health data, insurance healthcare data, or commercial healthcare data. The predetermined criterion is the risk of death in a predetermined time frame. The results set identifies patients eligible for or needing end of life care. The system identifies patients at risk of death. The system may also identify patients who are predicted to die within a predetermined time frame.

Yet another embodiment discloses a system for establishing factors for a healthcare predictive model, comprising: a set of distinct variables used for statistical analysis, wherein the variables are representative of medical conditions of patients; a first module configured to identify a plurality of individual factors predictive of a certain outcome, based on a set of distinct variables; a second module configured to identify combination sets of the individual factors and test the combination sets for performance against one or more population sets; a third module configured to determine one or more combination sets meeting a criteria, wherein the third module comprises one or more neural networks; and a fourth module configured to apply a selected neural network against medical condition data of a pre-determined population of patients. The medical condition data comprises government health data, insurance data, or commercial healthcare data. The criteria to determine the selection of combination sets comprises identifying combination sets with a high correlation between patients who were predicted to have a high risk of death within a predetermined period of time and for which those patients did die. The system identifies patients eligible for or needing hospice care or other end of life care, and it also identifies patients who are predicted to die within a predetermined time frame. The system also comprises a testing module. The system is additionally configured to predict patient death within a pre-determined timeframe. One of the factors may comprise either a count of distinct durable medical equipment claims or a total amount paid for home health claims. One of the factors may comprise either a natural log of the payment for diagnosis related groups, or a natural log of skilled nursing facility charges. One of the factors may comprise a count of skilled nursing facility claims. One of the factors may comprise a factor selected from the group consisting of a count of skilled nursing facility claims, a count of distinct hospital visits with congestive heart failure diagnosis, a count of distinct claims with pain-related diagnoses, a member age, and a total amount paid for physician claims. The factors may comprise a count of skilled nursing facility claims and at least one factor selected from the group consisting of a count of distinct hospital visits with congestive heart failure diagnosis, a count of distinct claims with pain-related diagnoses, a member age, and a total amount paid for physician claims. One of the factors may comprise a factor selected from the group consisting of a count of distinct durable medical equipment claims, a total amount paid for home health claims, a natural log of the payment for diagnosis related groups and a natural log of skilled nursing facility charges.

And still another embodiment identifies a method of identifying patients at risk of death and eligible for end of life care, the method comprising: accessing and organizing a set of data comprising patient healthcare for a plurality of patients over a predetermined time period; and applying a predictive model to the set of data so as to identify any patients at risk of death in a next predetermined time period. The set of data is insurance claim data. The set of data can also be government health data. The method additionally comprises contacting patients having an estimated end of life status within a predetermined threshold to offer the patient end of life care including admission to a hospice. The appropriate action may also include being administered interventions related to end of life care. The predetermined time period may be a year. The predictive model estimates end of life risk by inputting patient data into a model configured to utilize factors that show the highest correlation of predicting death in a patient and wherein the patient did die within the prescribed time parameters. The predetermined time period is in a range of one day to about one year.

Another embodiment discloses a computer implemented system for identifying patients needing end-of-life care, the system comprising: a computing environment; a storage in data communication with the computing environment and configured to store patient data and a set of distinct factors; a software program operating on the computing environment and configured to: identify combination sets of individual factors predictive of a certain outcome and that have a high correlation in the patient data with the target outcome; execute a plurality of neural networks using the combination sets of individual factors; and select one of the plurality of the neural networks based on the results of executing the neural networks; apply the selected neural network to the patient data; and output a list of patients at risk for end of life within a predetermined period of time. The computer implemented system returns output identifying a group of patients identified as being at the end of life and eligible for end of life care. One of the factors comprises either a count of distinct durable medical equipment claims or a total amount paid for home health claims. One of the factors comprises either a natural log of the payment for diagnosis related groups, or a natural log of skilled nursing facility charges. One of the factors comprises a count of skilled nursing facility claims. One of the factors comprise a factor selected from the group consisting of a count of skilled nursing facility claims, a count of distinct hospital visits with congestive heart failure diagnosis, a count of distinct claims with pain-related diagnoses, a member age, and a total amount paid for physician claims. The factors comprise a count of skilled nursing facility claims and at least one factor selected from the group consisting of a count of distinct hospital visits with congestive heart failure diagnosis, a count of distinct claims with pain-related diagnoses, a member age, and a total amount paid for physician claims. One of the factors comprises a factor selected from the group consisting of a count of distinct durable medical equipment claims, a total amount paid for home health claims, a natural log of the payment for diagnosis related groups and a natural log of skilled nursing facility charges.

Yet another embodiment discloses a computer readable medium containing software that, when executed, causes the computer to perform the acts of: accessing and organizing a set of data comprising patient healthcare data for a plurality of patients over a predetermined time period; and applying a predictive model to the set of data so as to identify any patients at risk of death in a next predetermined time period.

Yet another embodiment describes a method of incrementally updating a set of factors for input to a predictive modeling program wherein the set of factors are indicative of patient healthcare records, the method comprising: choosing a first set of factors for input into the predictive modeling program; receiving output from the predictive models identifying patients at risk for death in a predefined period; determining, after the predefined time period has completed, which patients did die; comparing the factors with the outcome data to determine which factors achieved the greatest accuracy; and adjusting the factor set based on the outcome results periodically. The adjustment of the factors may be done annually. The factors may comprise a count of the number of hospital stays and length of the hospital stays for a patient. The predetermined period is used for predicting end of life, for example, within one year. One of the factors may comprise a count of skilled nursing facility claims. The factors may comprise one or more factors selected from the group consisting of a count of skilled nursing facility claims, a count of distinct hospital visits with congestive heart failure diagnosis, a count of distinct claims with select pain-related diagnoses, a member age as of end of year used in model, and a total amount paid for physician claims. The factors may comprise a count of skilled nursing facility claims and at least one factor selected from the group consisting of a count of distinct hospital visits with congestive hear failure diagnosis, a count of distinct claims with select pain-related diagnoses, a member age as of end of year used in model, and a total amount paid for physician claims. One of the factors may comprise a factor selected from the group consisting of a count of distinct durable medical equipment claims, a total amount paid for home health claims, a natural log of the payment for diagnosis related groups and a natural log of skilled nursing facility charges.

Another embodiment discloses a system for predicting end of life for a patient within a predetermined time frame using a set of predictive models, the system comprising: means for storing and executing a set of predictive models on a computing device; means for identifying factors which have a correlation to end of life as input to the models; means for updating the factor sets based on previous successful predictions of the models; and means for outputting a report identifying particular groups of patients meeting a certain criteria based on at least the identified factor sets. The report outputting means comprises a spreadsheet, list or other report identifying specific patients at risk for death within a specified time frame. The predictive models comprise configured neural net models. One of the factors may comprise either a count of distinct durable medical equipment claims or a total amount paid for home health claims. One of the factors comprises either a natural log of the payment for diagnosis related groups, or a natural log of skilled nursing facility charges. One of the factors may comprise a count of skilled nursing facility claims. One of the factors may comprise a factor selected from the group consisting of a count of skilled nursing facility claims, a count of distinct hospital visits with congestive heart failure diagnosis, a count of distinct claims with pain-related diagnoses, a member age, and a total amount paid for physician claims. The factors comprise a count of skilled nursing facility claims and at least one factor selected from the group consisting of a count of distinct hospital visits with congestive heart failure diagnosis, a count of distinct claims with pain-related diagnoses, a member age, and a total amount paid for physician claims. One of the factors may comprise a factor selected from the group consisting of a count of distinct durable medical equipment claims, a total amount paid for home health claims, a natural log of the payment for diagnosis related groups and a natural log of skilled nursing facility charges.

And yet another embodiment discloses a system for predicting end of life for a patient within a predetermined time frame from the output of a set of configured predictive models, the system comprising: a storage component; a software program configured to: identify factors as input into the models; update the factors based on previous successful predictions of the models; and output a report identifying a particular group of patients meeting a certain criteria based on at least the identified factors. One of the factors may comprise a count of skilled nursing facility claims. One of the factors comprise a factor selected from the group consisting of a count of distinct hospital visits with congestive heart failure diagnosis, a count of distinct claims with select pain-related diagnoses, a member age as of end of year used in model, and a total amount paid for physician claims. The factors may comprise a count of skilled nursing facility claims and at least one factor selected from the group consisting of a count of distinct hospital visits with congestive heart failure diagnosis, a count of distinct claims with select pain-related diagnoses, a member age as of end of year used in model, and a total amount paid for physician claims. One of the factors may comprise a factor selected from the group consisting of a count of distinct durable medical equipment claims, a total amount paid for home health claims, a natural log of the payment for diagnosis related groups and a natural log of skilled nursing facility charges.

BRIEF DESCRIPTION OF THE DRAWINGS

FIG. 4 is diagram of an example of a factor set for some embodiments of the End of Life Predictive Model.

DETAILED DESCRIPTION OF CERTAIN PREFERRED EMBODIMENTS

Figure 1:
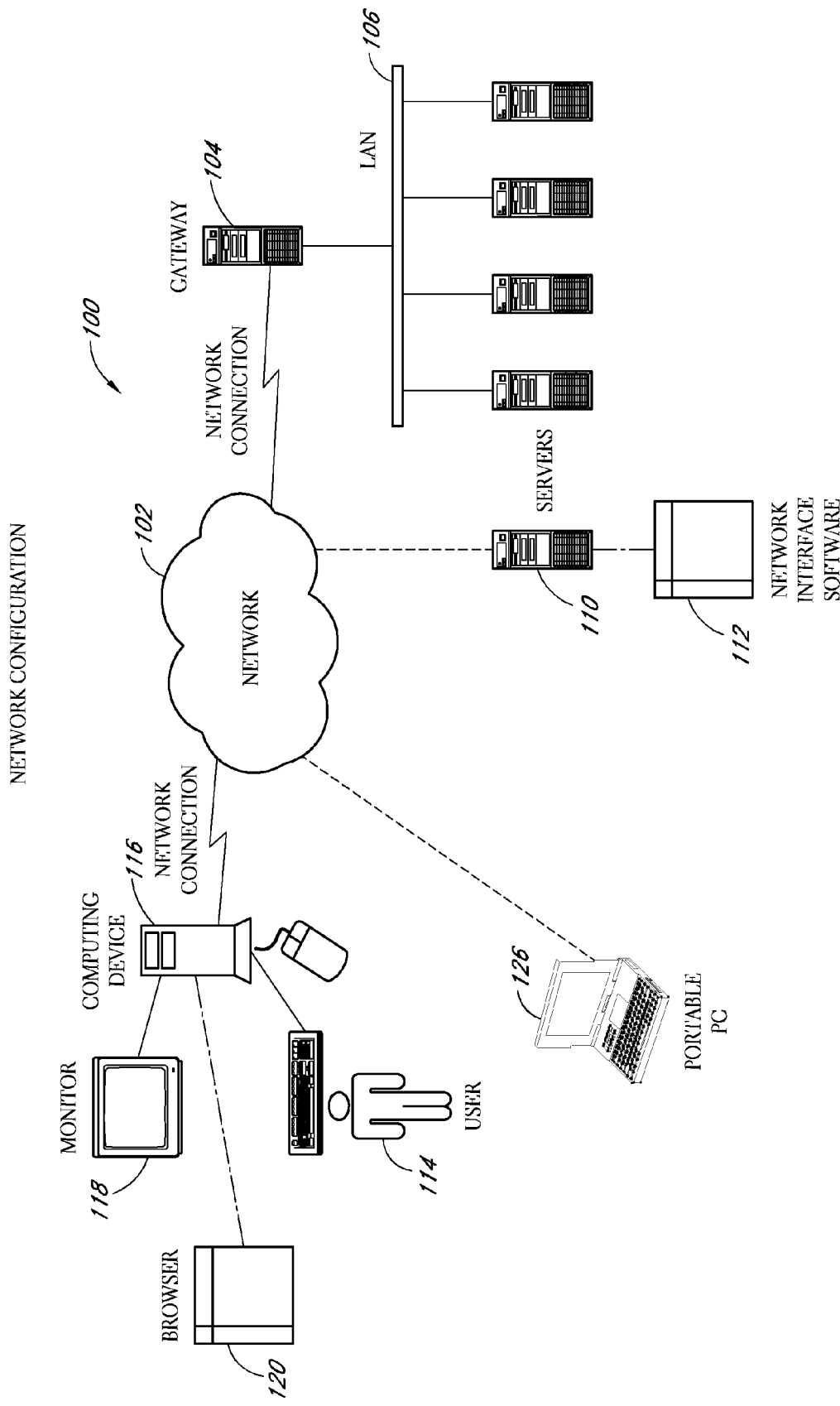
FIG. 1 is a block diagram of an example of a possible network that can be used to generate the predictive model program.

The following detailed description of certain embodiments presents various descriptions of specific embodiments of the invention. However, the invention can be embodied in a multitude of different ways as defined and covered by the claims. In this description, reference is made to the drawings wherein like parts are designated with like numerals throughout.

The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

The system is comprised of various modules, tools, and applications as discussed in detail below. As can be appreciated by one of ordinary skill in the art, each of the modules may comprise various sub-routines, procedures, definitional statements and macros. Each of the modules are typically separately compiled and linked into a single executable program. Therefore, the following description of each of the modules is used for convenience to describe the functionality of the preferred system. Thus, the processes that are undergone by each of the other modules may be arbitrarily redistributed to one of the other modules, combined together in a single module, or made available in, for example, a shareable dynamic link library.

The system modules, tools, and applications may be written in any programming language. For example, in some embodiments, the applications may be written in C, C++, BASIC, Visual Basic, Pascal, Adam, Java, HTML, XML, or FORTRAN, and executed on an operating system. In some embodiments, the operating system may be Windows, Macintosh, UNIX, Linux, VxWorks, or another variant of the foregoing operating system. C, C++, BASIC, Visual Basic, Pascal, Ada, Java, HTML, XML and FORTRAN are industry standard programming languages for which many commercial compilers can be used to create executable code.

Some configurations of the system and method provide a report containing actual names and contact information for patients who are identified as having the highest risk of death in a predetermined time period.

Some configurations of the system and method utilize protected data. This data is held in conformance with HIPAA regulations for the protection of health information.

Some configurations of the system and method utilize a multi-tier application architecture where the presentation, application, and/or data layers are separate but interoperable, allowing for a high degree of scalability, maintainability and customization to meet the needs of a healthcare organization.

The system is a computer implemented system which performs predictive modeling using a combination of neural network models and statistical models, to predict a certain health outcome related to a patient's healthcare, within a certain amount of time and selected from a group of patients. The predictive modeling system accepts operator-defined factor sets which run against populations of input data and are updated over time on a semi-regular basis. The predictive modeling system utilizes groups of linear and nonlinear selection techniques such as logistic regression models, chi square associations, r-squared associations, and decision tree modeling. Another type of predictive modeling tool is a neural network which is a non-linear statistical data modeling or decision making tool. These types of models can be used to model complex relationships between inputs and outputs or to find patterns in data.

The formatted data is divided into groups, in some embodiments, three groups, and is ready for input into the statistical models. The predictive model system includes statistical models and neural net models. The data is first put through a set of statistical models which establish predictive values meeting predetermined criterion and then the selected factors are used to build a first set of neural net models, and the data is run against these models. The data is then run through a second set of neural net models which are configured to receive this data from the first set of neural network models. The strongest neural networks are identified and compared against each other until a final model is identified for which to run the input data and generate the output identifying the targeted group of patients.

Referring to FIG. 1, a block diagram of an example embodiment of a system configuration 100 will be described. The system 100 includes a network "cloud" 102, which may represent a local area network (LAN), a wide area network (WAN), the Internet, or another connection service.

The programs and databases used by the predictive model preferably reside on a group of servers 108 that are preferably interconnected by a LAN 106 and a gateway 104 to the network 102. Alternatively, the programs and databases may reside on a single server 110 that utilizes network interface hardware and software 112.

The network 102 may connect to a user computer 116, for example, by use of a modem or by use of a network interface card. The computer 116 can be any type of computing device that has a processor and a data communication capability, such as an IBM-compatible personal computer, an Apple MacIntosh, or various other computing devices. A user 114 at computer 116 may utilize a browser 120 to remotely access the programs using a keyboard and/or pointing device and a visual display, such as a monitor 118. Alternatively, the browser 120 is not utilized when the programs are executed in a local mode on computer 116, or when the computer is used as a terminal.

Various other devices may be used to communicate with the servers 108/110. Other connection devices for communicating with the server 108/110 include a portable personal computer with a modem or wireless connection interface. Other ways of allowing communications between the user 114 and the servers 108/110 are envisioned.

Figure 2A:
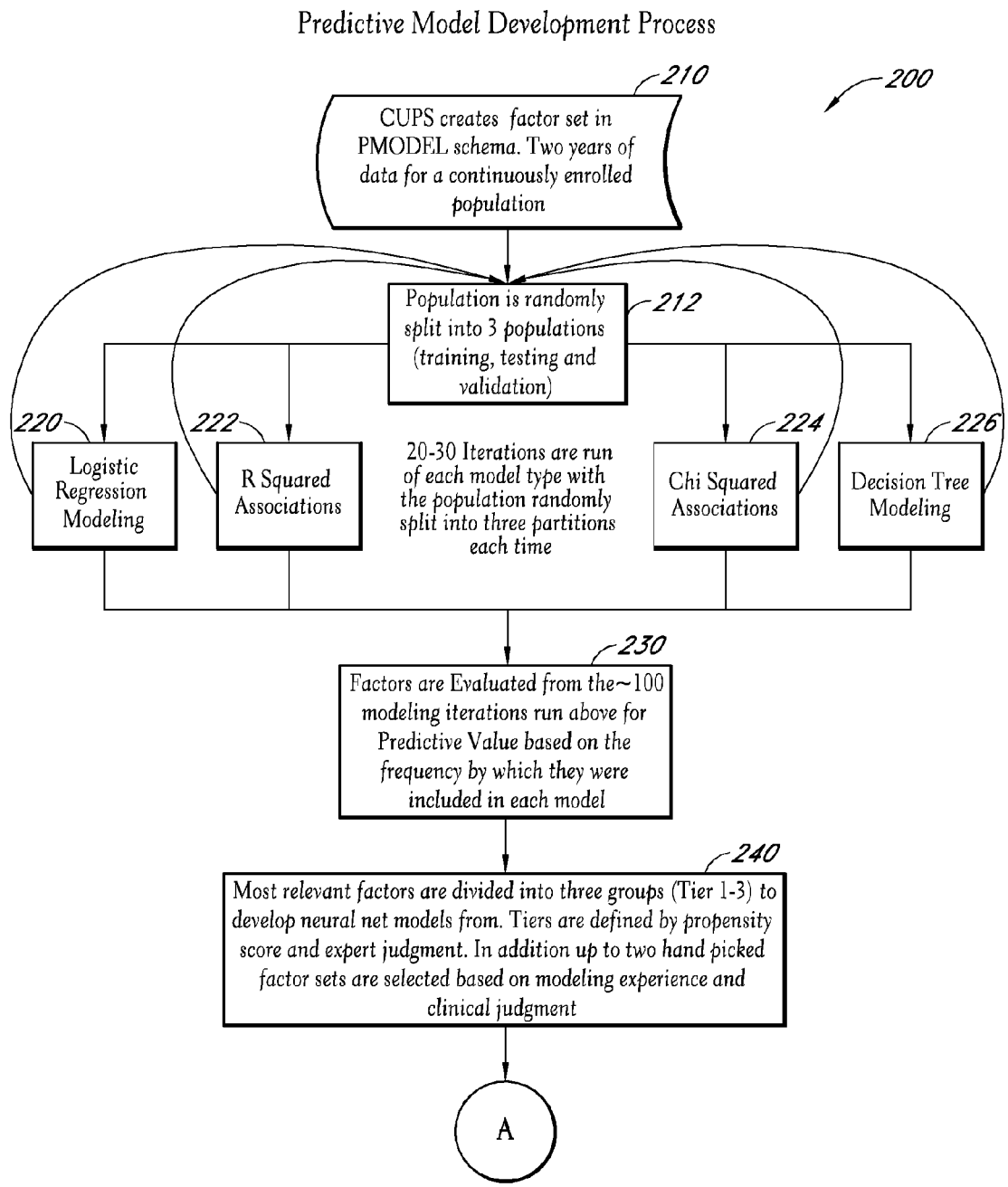
FIGS. 2A and 2B are flowcharts of an example process to develop the End of Life Predictive Model.
Figure 2B:
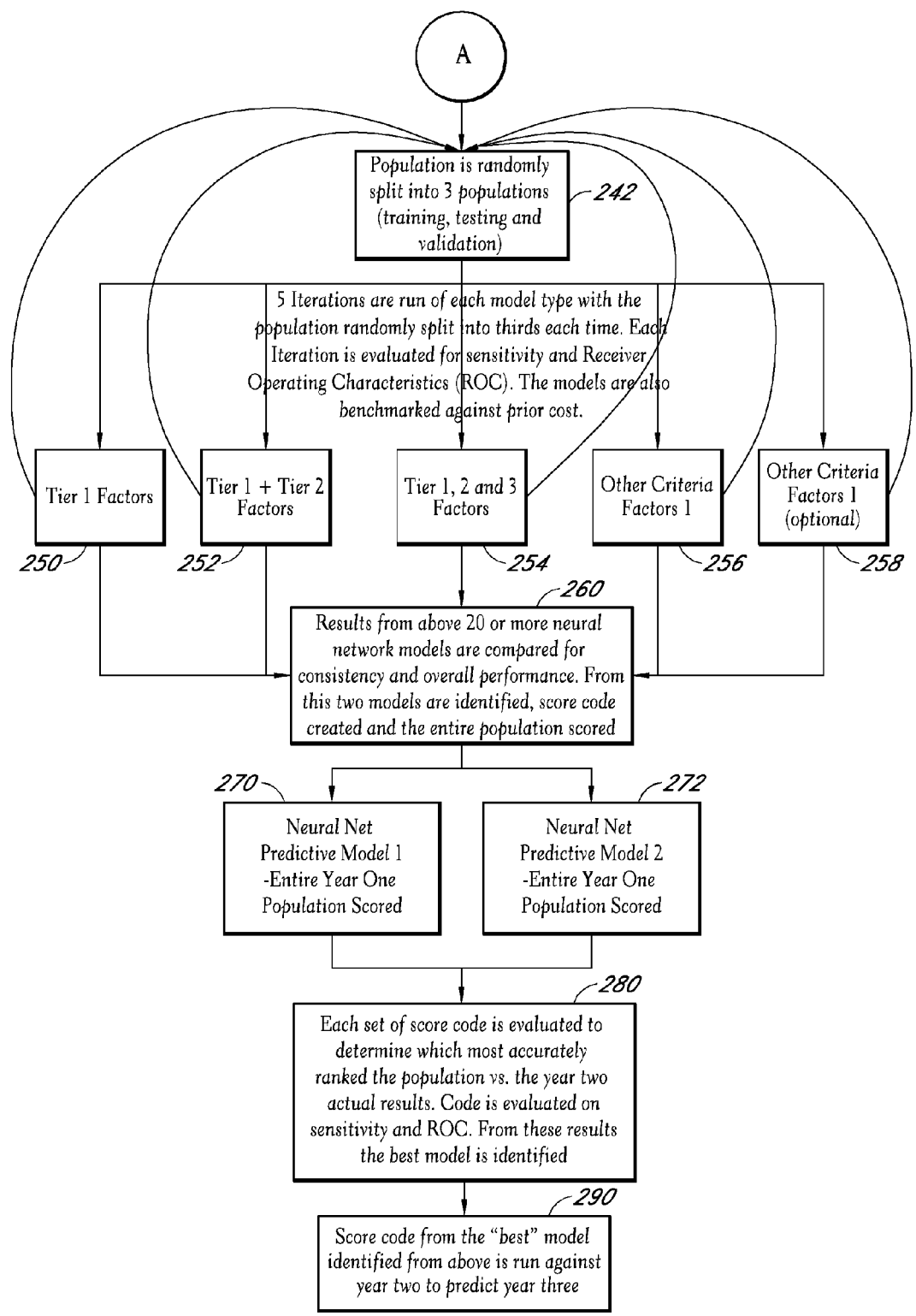

Referring to FIGS. 2a and 2b, one embodiment of a process 200 will be described using the End of Life Predictive Model ("EOL-PM"), as one example. Process 200 provides a certain sequence of processes, but in other embodiments, other groupings of processes may be contemplated. The process 200 begins by identifying the target outcome that is desired to be predicted. In some embodiments, the target is the risk of death to a group of patients, the risk being within a predetermined timeframe. The target is defined, and the appropriate input data source is identified. Input data is supplied by a source that has access to very large repositories of healthcare-related data. In certain embodiments, a large government agency in possession of patient healthcare data is the source of the input data, and it may consist of healthcare claims and eligibility data. For example, in some embodiments, the data may be data relating to Medicare claims and eligibility. In other embodiments, the data may be data from an insurance provider. In certain embodiments, the target outcome for the EOL-PM is death in the target year and is determined by eligibility data received from the government agency for program members. Data variables representative of medical conditions of patients, with a potential relationship to the target are selected to identify factors predictive of a certain outcome. For example, in some embodiments, the data variables may include one or more of the following factors: Count of Skilled Nursing Facility Claims, Count of Distinct Hospital Visits with Congestive Heart Failure (CHF) Diagnosis, Count of Distinct Claims with Select Pain Related Diagnoses, Member Age as of End of Year Used in Model, Total Amount Paid for Physician Claims, Change in Total Dollars from the First Half of the Year to Total Dollars from the Second Half of the Year, Count of Distinct Emergency Room (ER) Visits with Congestive Heart Failure Diagnosis, Count of Distinct Hospital Visits with Diabetes Diagnosis, Count of Distinct Durable Medical Equipment Claims, Total Amount Paid for Home Health Claims, Total Amount Paid for All Claims, Change in Count of Distinct Hospital Visits with Congestive Heart Failure Diagnosis from the First Half of the Year to the Count from the Second Half of the Year. Natural Log of the Payment for Diagnosis Related Groups, Change in Outpatient Charges from the First Half of the Year to Outpatient Charges from the Second Half of the Year, Natural Log of Skilled Nursing Facility Charges, ID to Identify Unique Claim, Internal Indicator of Type of Visit, Internal Indicator of Place of Service, Discharge Date, Date Indicating Last Date of Service on Claim, Admission Date, Date Indicating First Date of Service on Claim, ICD Diagnosis Codes in Positions 1-11, Date of Birth, Provider Specialty Code as Defined by CMS, Internal Indicator for Total Dollars, Total Dollars on Claim, Internal Indicator of Count of Congestive Heart Failure Hospital Visit Claims, Total Payment for Diagnosis Related Groups, Internal Indicator for Total Outpatient Dollars, Total Amount Paid for Skilled Nursing Facility Claims. These factors are selected from eligible data based on criteria appropriate for the target which is being predicted. The process uses a factor set which consists of many factors, for example approximately 150 factors, developed largely from claims, demographic, and program data. Because there is a large variance between health plans, diseases, outcomes, and diagnoses, the factor set must be broad enough to be useful across multiple inputs. At the same time, each factor needs to have some anticipated or demonstrated value with respect to predictions. This value of each factor, alone and in a factor set is repeatedly measured in different predictive modeling scenarios. Additionally, the appropriate data sources are identified based on the definition of each factor. For example, the appropriate data source for inpatient admissions is hospital claims data, whereas the appropriate data source for member age is member-level demographic data. A factor set for one embodiment is found in FIG. 4.

Now referring to FIG. 4, a description of the factor sets and their utilization in the predictive models will be described.

Each predictive model utilizes a particular set of factors in its various statistical models and neural network models. The specific factor sets are selected from a greater pool of factor sets to be effective in predicting the target, and, of course they will vary depending on the target that is predicted. As the statistical models run populations of data, the predicted output can be compared against actual data withheld from the modeling process which was run through the model for the purpose of validation. This process identifies the factors that are the most relevant when predicting the predetermined outcome. In some embodiments the predetermined outcome is the prediction of the risk of death. In this way, the final factor sets are developed and updated, as output data can be compared against actual data for analysis as to which factors achieved the greatest correlation with the target. The factors in FIG. 4 are the factors that, for example in this embodiment, are considered "top" factors in the predictive models. The top factors will be different for each model depending on the chosen target. As will be further explained, the factors are those criteria that have a high correlation to a specific indicator in the input data. For example, in one embodiment, the factors would correlate to indicators that are used to predict end of life for a patient. In some embodiments, there are three tiers identified as Tier 1, Tier 2, Tier 3, and whose application to the predictive model will be discussed in subsequent sections. In come embodiments, there are factors that are not identified by their performance in the statistical models. Review by analysts may identify factors having value, usually by the factor's inclusion in other models, the analyst's past experience, or other criteria. These factors are referred to as Other Criteria 256 and can be added to the factor sets to be included in the development of the neural net models.

In some embodiments, Tier 1 factors include one or more factors selected from the group consisting of a Count of Skilled Nursing Facility Claims, a Count of Distinct Hospital Visits with Congestive Heart Failure Diagnosis, a Count of Distinct Claims with Select Pain-Related Diagnoses, a Member Age as of End of Year, and a Total Amount Paid for Physician Claims. In some embodiments, Tier 1 Factors include two or more, three or more or four or more factors selected from the group consisting of Count of Skilled Nursing Facility Claims, a Count of Distinct Hospital Visits with Congestive Heart Failure diagnosis, a Count of Distinct Claims with Select Pain-Related Diagnoses, a Member Age as of End of Year, and a Total Amount Paid for Physician Claims. In some embodiments, Tier 2 factors include Tier 1 factors and can include one or more factors selected from the group consisting of a Change in Total Dollars from the First Half of the Year to Total Dollars from the Second Half of the Year, a Count of Distinct Emergency Room Visits with Congestive Heart Failure Diagnosis, a Count of Distinct Hospital Visits with Diabetes Diagnosis, a Count of Distinct Durable Medical Equipment Claims, and a Total Amount Paid for Home Health Claims. In some embodiments, Tier 2 factors include two or more, three or more, or four or more factors selected from the group consisting of a Change in Total Dollars from the First Half of the Year to Total Dollars from the Second Half of the Year, a Count of Distinct Emergency Room Visits with Congestive Heart Failure Diagnosis, a Count of Distinct Hospital Visits with Diabetes Diagnosis, a Count of Distinct Durable Medical Equipment Claims, and a Total Amount Paid for Home Health Claims. In some embodiments, the Tier 3 factors include the Tier 1 and Tier 2 factors, and include one or more factors selected from the group consisting of Total Amount Paid for All Claims, Change in Count of Distinct Hospital Visits with cCongestive Heart Failure diagnosis from the First Half of the Year to the Count for the Second Half of the Year, Natural Log of the Payment for Diagnosis Related Groups, Change in Outpatient Charges from the First Half of the Year to Outpatient Charges for the Second Half of the Year, and Natural Log of Skilled Nursing Facility Charges. Tier 3 factors include two or more, three or more, or four or more factors selected from the group consisting of a Total Amount Paid for All Claims, Change in Count of Distinct Hospital Visits with Congestive Heart Failure Diagnosis from the First Half of the Year to the Count for the Second Half of the Year, Natural Log of the Payment for Diagnosis Related Groups, Change in Outpatient Charges from the First Half of the Year to Outpatient Charges for the Second Half of the Year, and Natural Log of Skilled Nursing Facility Charges. FIG. 4 shows the Tier 1, Tier 2 and Tier 3 factors for these embodiments. In other embodiments, the top factors may be different.

Referring to FIG. 4, a factor description chart 400, a chart of factors for input to the predictive model, is described herein. In some embodiments, the textual abbreviations used to designate the factors may be suggestive of the type of data included in the factors. Alternatively, the textual abbreviations may have no correlation to the type of data included. For instance, in this embodiment, the first column 410 contains patient healthcare data field names. In some embodiments, factor names correspond to the data field name they represent in the predictive model system. In the middle column 420, descriptions of the factor names in plain language are found. Column 430 describes the processing rules for each factor 410 and in some embodiments, additional codes are listed that are indicative of other information, such as insurance codes. In some embodiments, these rules 430 are the acronyms and computer rules which are pertinent to the logic of the predictive models. The meanings of the numeric codes used in rules 430 may be obtained from the International Classification of Diseases established by the American Medical Association. These codes are available for example in ICD-9-CM 2008, Volumes 1, 2, 3, the disclosures of which are incorporated herein by reference in their entireties. Another source of this information may include the AMA website. For example, a factor name 410 may be indicative of a patient record field which could be ten characters long, the field defined by the rules 430 and comprising codes that indicate the claim identification, the hospital visited, and the codes from the source above, which indicate the diagnoses. In this embodiment, for example, the factors listed represent the Tier 1, Tier 2, and Tier 3 factors. The first five factors are Tier 1 factors, the Tier 1 plus the next five are Tier 2 factors, and the Tier 1, Tier 2, plus the last five are Tier 3 factors. However a given tier can contain as many factors as needed.

In some embodiments, some of these factors may be relatively simple (total baseline cost, age, gender), but others are more complex and consider the interaction and dependencies of multiple other factors. In some embodiments, these factors include a count of congestive heart failure-related emergency room claims, and the degree to which such a count is increasing or decreasing through the baseline year. Factors are periodically reviewed for predictive ability or tendencies. The identified factors are placed in a model development cycle to see if they fit a given application. In this way, the factor set is ever evolving. A suitable modeling population with data available for a period of time, in some embodiments a two year period, is identified from eligibility data based on criteria appropriate for the target to be predicted. In certain embodiments, the target population is a subsection of a given database of patient data, designated as program members, who are alive at the end of the first year. In some embodiments, input data records from which the target is garnered may consist of data contracted through a large repository entity, for example, such as Medicare.

Now referring again to FIGS. 2A and 2B, at a state 210, a data set is created with values for each of the factors for each member of the population. Input data enters the system through a staging area for the input data, an input data module. This module prepares the data by tabbing and labeling it to prepare it for the predictive modeling software. This input data module creates a factor set in the predictive model schema. The factor set consists of the factors as described above which have been selected based on their predictive ability. The factor set is the result of many iterations and analyses of predictive model system output. In some embodiments, the number of test iterations is thirty (30). Data for a continuously enrolled population is kept for a number of years, for example, two years. The end result is one population of data ready to be run through the remaining modules. Values for the factors are computed separately for the earlier of, for example, the two years from eligibility data based on criteria appropriate for the target to be predicted. The data set also includes a flag to indicate the presence or absence of the target outcome (for example, death in the target year).

The next states describe the process to pare down the original factor set by identifying a subset of factors with the strongest associations with the target. These factors are used in the development of neural net predictive models.

Proceeding to a state 212, a statistical analysis data mining software package, for example SAS software Enterprise Miner, is used to perform the model building described in the subsequent steps. The predictive modeling software is run on a computer system, such as server 110 or servers 108 (FIG. 1). The population is randomly split into one or more populations for training, testing, and validation, as appropriate, for the selection techniques in the next state. In some embodiments, the data is split into three (3) populations. The training data are used for preliminary model fitting. The validation data are used to evaluate the generalizability and goodness of fit of the models. The test data are available for model assessment. These selection techniques are employed to ultimately determine which factors are most repeatedly and consistently associated with the prediction of the target of interest. Multiple techniques are employed in order to find a robust set of factors that are deemed important regardless of the modeling or association technique used in the selection process. Data population is then randomly split into three groups: training, testing and validation. Moving to states 220 through 226, several types of predictive models are run. For example, in some embodiments, four types of predictive models are run. Any number or type of predictive models can be selected for this state, providing that the factors can be evaluated upon completion of a run cycle.

Process 200 advances to state 220 where, in certain embodiments, over thirty iterations of logistic regression models are run. In other embodiments, other numbers of iterations can be run. The population is partitioned for each iteration using random sampling (stratified when appropriate). The partitioning of the data is beneficial due to the iterative nature of logistic model development via the modeling software packages. Logistic models are developed on the training portion of the dataset and then their adequacies are examined via the validation portion of the dataset. These partitions of data are also stratified to ensure that the incidence of the target of interest is spread equally across the required partitions. For each iteration of logistic regression modeling, the factors deemed useful are compiled for factor selection at state 230. Useful factors are those which show the strongest associations with the target.

In certain embodiments, several iterations of R-square associations are run at state 222. In some embodiments over thirty iterations are run. R-square associations measure the strength of the correlation between the factor being considered and the target of interest. As described previously, the population is partitioned for each iteration using random sampling (stratified when appropriate). In the case of R-square associations, partitioning is not essential as it is not an iterative modeling technique. However, the software allows for simpler modeling diagrams and faster processing using samples of data, so the partitions are included.

In some embodiments, several iterations of chi-square associations are run at state 224. In some embodiments or systems, over thirty iterations of chi-square associations are run. Chi-square associations also measure the strength of the association between the factor being considered and the target of interest. As described previously, the population is partitioned for each iteration using random sampling (stratified when appropriate). In the case of chi-square associations, partitioning is not essential as it is not an iterative modeling technique. However, the software allows for simpler modeling diagrams and faster processing using samples of data, so the partitions are included.

Decision tree modeling at state 226 is preferably not used for the EOL-PM, because the relative infrequency of the presence of the target may reduce performance (the software utilized may not be find meaningful splits to create decision trees). However, decision tree modeling may be used in other embodiments.

The factors from the iterations run using each of the selection techniques at states 220-226 are evaluated at a state 230 for predictive value based on the frequency by which they are included in the selection techniques. An output is created disclosing the number of samples run for each selection technique and the count for each factor to represent the number of samples in which the factor displayed significant association with or predictive value of the target variable. In certain embodiments the output is a spreadsheet. The counts for each selection technique are summed for each factor to represent the total number of times the factor demonstrated association with the target across all selection techniques. The assumption is that the more often a factor is chosen, the more predictive ability it has relative to the target of interest. Often certain factors are deemed predictive across all modeling techniques and almost every iteration. On other occasions, a factor is deemed to have moderate predictive ability because it is selected in a majority of iterations for a given selection technique (and is hardly ever selected via the other techniques). In a case such as this, models may need to be built both with and without such a factor to determine if it is worth inclusion in a predictive model. In some embodiments, certain factors are not deemed predictive of the predetermined criteria through the iterations described in this paragraph. In these cases, an analyst may determine that the factor should be included based on such criteria as the factor's performance in past models, the analyst's prior experience, or other criteria. These factors may be included, as well as the factors identified by the models.

Using the output of these models at state 230, the data population is combined into one group. The factors that are identified at the beginning of the process are evaluated from the modeling iterations run above for predictive values based on the frequency by which they are included in each model. In some embodiments, the number of iterations run is over one hundred.

The most relevant factors are divided into several groups at state 240 from which to develop neural net models. In some embodiments, the most relevant factors are divided into three groups (for example, Tier 1, Tier 2, and Tier 3). Tiers are defined by overall score. Tier 1 typically includes the "top" five or six factors, Tier 2 typically includes the "top" ten to twelve factors, and Tier 3 typically includes the "top" fifteen to eighteen factors. Tier 2 factors are inclusive of Tier 1 factors; likewise, Tier 3 factors are inclusive of Tier 1 and Tier 2 factors. In addition, other factor sets may be selected for neural net modeling based on modeling experience and clinical relevance. The steps detailed above assist in fitting the model without over-fitting the model. The selection of various amounts of inputs with "suspect" factors both included and not included, allows pragmatic determination of which battery of factors allowed for the most accurate predictions. For example and illustrative of the methodology, factors such as age and medical expenditures are found to be correlated with likelihood of death, and factors such as a count of distinct pieces of durable medical equipment purchased are also found to be predictive. The techniques below allow consideration of various models built from various factor sets to determine which set of factors would ultimately yield the most predictive neural network predictive model. Using other criteria, factors are selected which may display only moderate association with the target but which may appear to have clinical or intuitive relevance. The "top" factors are those which are identified most frequently in the previous step as having association with the target.

The next sections describe the development of neural net models from which the strongest performer is selected for implementation.

The population is again randomly split at state 242 into several populations for training, testing, and validation, for the modeling techniques in the next state. For example, the population may be split into three populations in some embodiments. The training data are used for preliminary model fitting, and the validation data are used to evaluate the generalization and goodness of fit of the models. The test data are used to comparatively assess model performance with respect to identification of the target of interest.

Several iterations of neural network models are run at state 250 using the Tier 1 factors, with, the population randomly split into three partitions (training, validation, testing) each time using a random number seed. In some embodiments, these factors include, a skilled nursing facility count, and a count of diagnoses which begin with a specified three-character code. In some embodiments, five iterations are run. Each iteration of the modeling yields a model that is custom fit to the training and validation sets passed into the neural network node of the predictive modeling system. This programming in the models use iterative artificial intelligence techniques to create new models (per the training data) and ensure that models are adequate (per the validation data). The performances (per the testing data) of the neural network models created via each iteration and the average of the multiple rounds are evaluated for sensitivity and Receiver Operating Characteristics (hereinafter referred to as "ROC"). Sensitivity is defined as the percentage of the target correctly captured by the model. The ROC is a measure of the fit of the model, defined as a function of the sensitivity compared to the specificity of the model at different screening thresholds. Specificity is defined as the percentage not meeting the target correctly identified by the model. This process is designed to ensure the development of robust, ever-improving neural network predictive models. Repeated development across multiple data partitions demonstrates which models consistently perform well across different populations.

Several iterations (with methods similar to those described in State 250) of neural network models are run at state 252 using the Tier 2 factors (inclusive of Tier 1 factors), with the population randomly split into three partitions (training, validation, testing) each time using a random number seed. In some embodiments, the Tier 2 factors include the count of certain hospital charges, diagnoses codes, and durable medical equipment costs. In some embodiments, five iterations are run. Each iteration and the average of the multiple rounds are evaluated for sensitivity and Receiver Operating Characteristics (ROC). Sensitivity is defined as the percentage of the target correctly captured by the model. The ROC is a measure of the fit of the model, defined as a function of the sensitivity compared to the specificity of the model at different screening thresholds. Specificity is defined as the percentage not meeting the target correctly identified by the model. This process is designed to ensure the development of robust, ever-improving neural network predictive models. Repeated development across multiple data partitions demonstrates which models consistently perform well across different populations.

Several iterations (with methods similar to those described at state 250) of neural network models are run at state 254 using the Tier 3 factors (inclusive of Tier 1 and 2 factors), with the population randomly split into three partitions (training, validation, testing) each time using a random number seed. In some embodiments, the Tier 3 factors include the count of certain hospital charges paid, diagnosis related group codes, and outpatient charges. In some embodiments, five iterations are run. Each iteration and the average of the multiple rounds are evaluated for sensitivity and Receiver Operating Characteristics (ROC). Sensitivity is defined as the percentage of the target correctly captured by the model. The ROC is a measure of the fit of the model, defined as a function of the sensitivity compared to the specificity of the model at different screening thresholds. Specificity is defined as the percentage not meeting the target correctly identified by the model. This process is designed to ensure the development of robust, ever-improving neural network predictive models. Repeated development across multiple data partitions demonstrates which models consistently perform well across different populations.

Several iterations (with methods similar to those described in state 250) of neural network models are run at state 256 using the other criteria factors, with the population randomly split into three partitions (training, validation, testing) each time using a random number seed. In some embodiments, five iterations are run. Each iteration and the average of the multiple rounds are evaluated for sensitivity and Receiver Operating Characteristics (ROC). Sensitivity is defined as the percentage of the target correctly captured by the model. The ROC is a measure of the fit of the model, defined as a function of the sensitivity compared to the specificity of the model at different screening thresholds. Specificity is defined as the percentage not meeting the target correctly identified by the model. This process is designed to ensure the development of robust models. Repeated development across multiple data partitions demonstrates which models consistently perform well across different populations.

A second factor set made up of other criteria at state 258 is preferably not evaluated for the End of Life PM, but may be evaluated in other embodiments.

Results from the neural network models are compared at state 260 for consistency and overall performance. In certain embodiments, twenty neural network models are compared, such as from states 250 to 256. From this, a final number of factor sets whose models consistently display the best performance are identified. In most embodiments, the final number is two factor sets. For example, in a recalibrated model, the Tier 3 factor set and other criteria factor set display the best performance. The recalibrated model is discussed below. The final neural net score code is created for each of the two factor sets. Having the score code (the logic containing the mathematical form of the predictive model) allows for direct comparison of the performance of the models against one another within the complete modeling population (or other populations if such are deemed necessary or of particular interest).

Using the above example, the modeling dataset is scored for the entire population at state 270 using the neural net model using the Tier 3 factors, creating a score for each member to indicate predicted risk of the target in, for example year two. In other embodiments a time period other than two years may be used.

Using the above example, the modeling dataset is scored for the entire population at state 272 using the neural net models using factors based on criteria other than the Tier 1, Tier 2 or Tier 3 factors. In some embodiments, a time period other than two years may be used. In yet other embodiments, the models with the two best performances are scored and compared.

The models from the previous states 270 and 272 are compared directly across the entire modeling population at state 280 to determine which models most accurately ranked the population input data as compared to the actual results over a period of time, in some embodiments, the period of time being two years. The models are evaluated with respect to sensitivity and ROC. From these results the best model is identified as that having the greatest sensitivity and ROC.

The best model is then selected and implemented at state 290.

Factor sets are improved and updated by analyzing the factors as they perform in the testing and validation models. The relative merit of each factor can be repeatedly manually evaluated in addition to the neural networks ability to pick the most relevant factors. By scoring against actual data of death occurrences of the previous identified patient lists, the factor sets and models and can be adjusted for more relevant results. This process is referred to as recalibrating the model, which is periodically done to make the model fit the evolving healthcare realities of the membership under consideration. Membership refers to the source of the input data. In some embodiments, this is Medicare.

Figure 3:
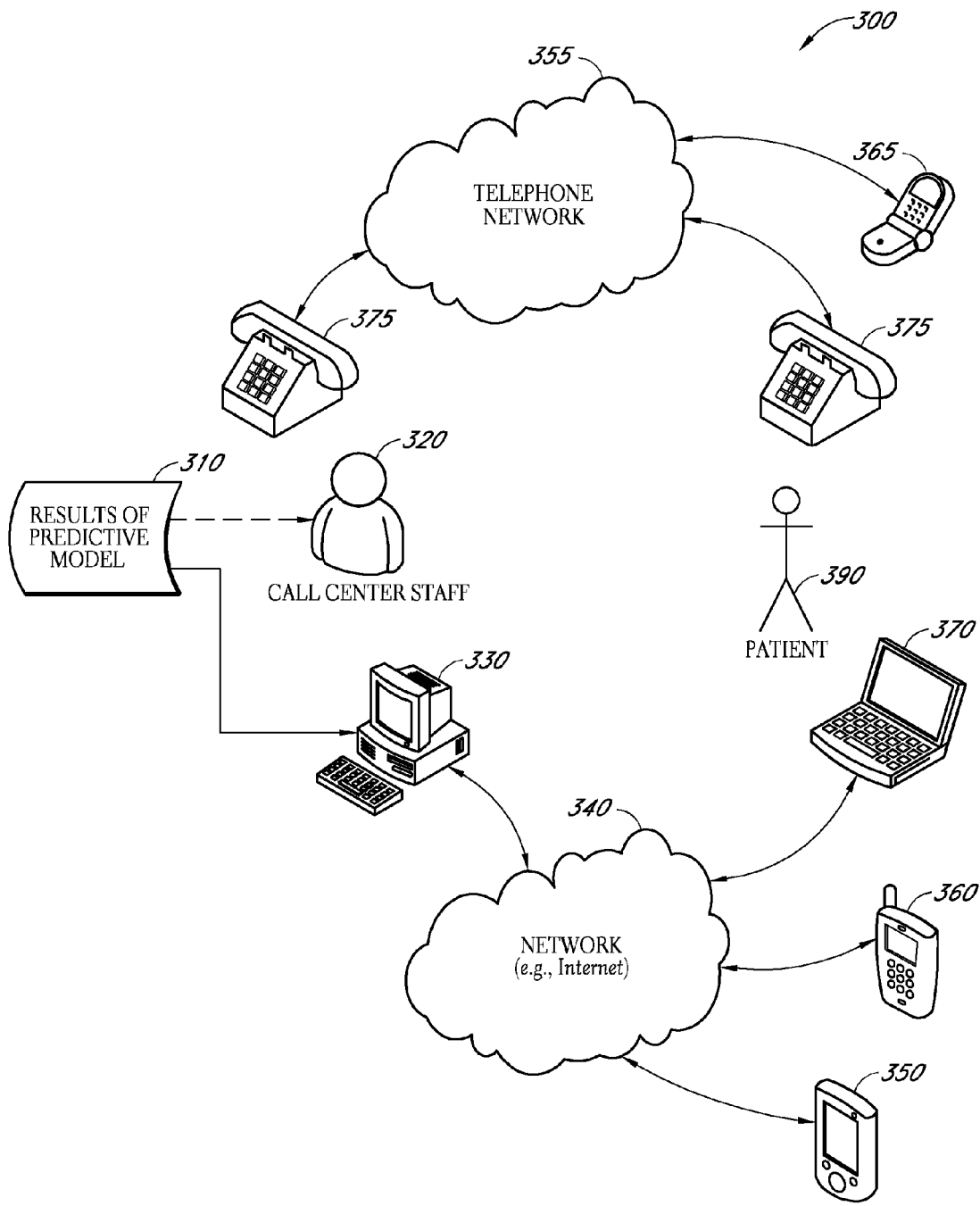
FIG. 3 is a block diagram of an example configuration for utilizing the results of the End of Life Predictive Model.

Now referring to FIG. 3, an example of how the results from the EOL-PM may be utilized, will be described. Results 310 of the predictive modeling process 200 (FIGS. 2a and 2b) are output for use in an end-user group. In some embodiments this can be a spreadsheet or report with name and contact information of patients who are identified as being at end of life. In some embodiments, the end user is a call center staff 320. In other embodiments, the results of the predictive modeling system 310 are sent to a computer system 330 which is capable of distributing it further over a network 340 such as the Internet. In some embodiments, information is received by a healthcare manager based on the results of the model, and who communicates the information to the patients 390. In some embodiments, the healthcare managers receive information electronically via, for instance, a mobile or cellular phone 360, a Personal Digital Assistant (PDA) or Smartphone 350, or an email or other message to a computer 370. In still other embodiments, the results of the predictive modeling system may be communicated entirely orally. In other embodiments, the call center staff 320 will receive the results and use a telephone network 355 to contact the patient 390 via mobile phone 365 or telephone 375, and arrange end of life care. In other embodiments, the patient can receive from the healthcare manager the results along with information about end of life care via a, mobile device, PDA, email or other electronic methods. In some embodiments, follow up care is communicated by any of the foregoing methods.

Some aspects of the system and method provide a method for supplying healthcare information. This method includes operating a server to communicate with one or more networks to obtain raw input data. The method further includes at least one statistical model each using one or more parameters, wherein the models are configured to determine statistical outcomes of a patient, and is further determined to be at the end of life. The method further includes parameter lists with reduced redundancy sufficient to apply the requested statistical models to produce model results and with default values of parameters when such default values are available, to receive and reformat the parameter lists and default values, when available, for transmission to end users or their agents as queries, to transmit information received in response to the queries to the server for processing in the requested models, to receive statistical results from the models, and to reformat the results and transmit the reformatted results to the end users or their agents.

In another aspect, the system and method provides a method for risk-stratifying individual patients. In this aspect, the method includes creating statistical health models configured to provide model results including patient risk assessments using healthcare data, such as Medicare data. In addition, the method includes operating a server to store data, the models, the factors, the results, and to apply a redundancy reduction procedure to the factors. The method further includes transmitting results from the analysis to another group of people, such as a call center.

In another embodiment, the system and method provides a statistical processing system. The statistical processing system includes one or more servers configured with program instructions implementing a plurality of statistical models to predict a health status outcome based on data inputs relevant to a particular population and patient. The system can further include a visual interface communicated by the server. The server is configured to analyze requests received from users relating to a plurality of the statistical models to reduce redundancy in requests for patient data.

It will thus be appreciated that configurations of the system and method provide systems and methods for analyzing medical information by comparing the medical information against statistically validated studies to make a proactive recommendation in the form of a risk assessment for patients at the end of life. Methods and apparatus of the system and method have the capacity to rapidly disseminate assessments in a variety of formats and to be updatable as new information becomes available. Thus, some configurations of the system and method provide assurance that the most accurate models can be provided for use at all times. Information provided can be used by providers to make informed decisions about patient care. Therefore, configurations of the system and method can help maximize the potential benefit from a particular intervention procedure and allow selection of the best of several alternative procedures.

While specific blocks, sections, devices, functions and modules may have been set forth above, a skilled technologist will realize that there are many ways to partition the system, and that there are many parts, components, modules or functions that may be substituted for those listed above.

While the above detailed description has shown, described, and pointed out the fundamental novel features of the invention as applied to various embodiments, it will be understood that various omissions and substitutions and changes in the form and details of the system illustrated may be made by those skilled in the art, without departing from the intent of the invention.

What is claimed is:

1. A system for identifying patients needing healthcare, comprising:
    a first module, executed by a processor, for preparation of patient data for input to statistical modeling submodules;
    a second module, executed by the processor, for receiving and evaluating outcome data of the statistical modeling submodules and establishing one or more predictive values meeting a predetermined criteria and applying the one or more predictive values to a first set of neural net models; and
    a third module, executed by the processor, configured to receive and apply one or more results from the first set of neural net models to a second set of neural net models and generate a results set indicative of patients needing healthcare,
    wherein the patient data comprises data from a pre-determined population set.

2. The system of claim 1, wherein the patient data is government health data, insurance healthcare data, or commercial healthcare data.

3. The system of claim 1, wherein the predetermined criteria is the risk of death in a predetermined time frame.

4. The system of claim 1, wherein the results set identifies patients eligible for or needing end of life care.

5. The system of claim 1, wherein the system identifies patients eligible for or needing hospice care or other end of life care.

6. The system of claim 1, wherein the system identifies patients who are predicted to die within a predetermined time frame.

7. A system for establishing factors for a healthcare predictive model, comprising:
    a processor; and
    a storage in data communication with the processor, such storage configured to store:
        a set of distinct variables used for statistical analysis, wherein the variables are representative of medical conditions of patients;
        a first module configured to identify a plurality of individual factors predictive of a certain outcome, based on a set of distinct variables;
        a second module configured to identify combination sets of the individual factors and test the combination sets for performance against one or more population sets;
        a third module configured to determine one or more combination sets meeting a criteria, wherein the third module comprises one or more neural networks; and
        a fourth module configured to apply a selected neural network against medical condition data of a pre-determined population of patients.

8. The system of claim 7, wherein the medical condition data comprises government health data, insurance data, or commercial healthcare data.

9. The system of claim 7, wherein the criteria to determine the selection of combination sets comprises identifying combination sets with a high correlation between patients who were predicted to have a high risk of death within a predetermined period of time and for which those patients did die.

10. The system of claim 7, wherein the system identifies patients eligible for or needing hospice care or other end of life care.

11. The system of claim 7, wherein the system identifies patients who are predicted to die within a predetermined time frame.

12. The system of claim 7, wherein the system is additionally comprised of a testing module.

13. The system of claim 7, wherein the system is additionally configured to predict patient death within a pre-determined timeframe.

14. The system of claim 7, wherein one of the factors comprises either a count of distinct durable medical equipment claims or a total amount paid for home health claims.

15. The system of claim 7, wherein one of the factors comprises either a natural log of the payment for diagnosis related groups, or a natural log of skilled nursing facility charges.

16. The system of claim 7, wherein one of the factors comprises a count of skilled nursing facility claims.

17. The system of claim 7, wherein one of the factors comprise a factor selected from the group consisting of a count of skilled nursing facility claims, a count of distinct hospital visits with congestive heart failure diagnosis, a count of distinct claims with pain-related diagnoses, a member age, and a total amount paid for physician claims.

18. The system of claim 7, wherein the factors comprises a count of skilled nursing facility claims and at least one factor selected from the group consisting of a count of distinct hospital visits with congestive heart failure diagnosis, a count of distinct claims with pain-related diagnoses, a member age, and a total amount paid for physician claims.

19. The system of claim 7, wherein one of the factors comprises a factor selected from the group consisting of a count of distinct durable medical equipment claims, a total amount paid for home health claims, a natural log of the payment for diagnosis related groups and a natural log of skilled nursing facility charges.

20. A method of identifying patients in need or eligible for hospice care or other end of life care, the method comprising:
   accessing, with a processor, a set of data stored in a storage, such data comprising patient healthcare for a plurality of patients over a predetermined time period;
   organizing the set of data with the processor;
   applying a predictive model, with the processor, to the set of data so as to identify any patients at risk of death in a next predetermined time period; and
   contacting patients having an estimated end of life status within a predetermined threshold to offer the patient end of life care.

21. The method of claim 20, wherein the set of data is insurance claim data.

22. The method of claim 20, wherein the set of data is government health data.

23. The method of claim 20, further comprising determining, based on the predictive model, that an appropriate action for at least one patient is to be admitted to a hospice.

24. The method of claim 20, further comprising determining, based on the predictive model, that an appropriate action for at least one patient is to be administered interventions related to end of life care.

25. The method of claim 20, wherein the predetermined time period is a year, and wherein the predictive model estimates end of life risk by inputting patient data into a model configured to utilize factors that show the highest correlation of predicting death in a patient and wherein the patient did die within the proscribed time parameters.

26. The method of claim 20, wherein the predetermined time period is in a range of one day to about one year.

27. A computer implemented system for identifying patients needing end-of-life care, the system comprising:
   a computing environment;
   a storage in data communication with the computing environment and configured to store patient data and a set of distinct factors;
   a software program operating on the computing environment and configured to:
      identify combination sets of individual factors predictive of a certain outcome and that have a high correlation in the patient data with the target outcome;
      execute a plurality of neural networks using the combination sets of individual factors;
      select one of the plurality of the neural networks based on the results of executing the neural networks;
      apply the selected neural network to the patient data;
      output a list of patients at risk for end of life within a predetermined period of time; and
      recommend end of life care for a group of patients identified as being at the end of life.

28. The system of claim 27, wherein one of the factors comprises either a count of distinct durable medical equipment claims or a total amount paid for home health claims.

29. The system of claim 27, wherein one of the factors comprises either a natural log of the payment for diagnosis related groups, or a natural log of skilled nursing facility charges.

30. The system of claim 27, wherein one of the factors comprises a count of skilled nursing facility claims.

31. The system of claim 27, wherein one of the factors comprise a factor selected from the group consisting of a count of skilled nursing facility claims, a count of distinct hospital visits with congestive heart failure diagnosis, a count of distinct claims with pain-related diagnoses, a member age, and a total amount paid for physician claims.

32. The system of claim 27, wherein the factors comprises a count of skilled nursing facility claims and at least one factor selected from the group consisting of a count of distinct hospital visits with congestive heart failure diagnosis, a count of distinct claims with pain-related diagnoses, a member age, and a total amount paid for physician claims.

33. The system of claim 27, wherein one of the factors comprises a factor selected from the group consisting of a count of distinct durable medical equipment claims, a total amount paid for home health claims, a natural log of the payment for diagnosis related groups and a natural log of skilled nursing facility charges.

34. A server storing software that, when executed, performs the acts of:
   accessing and organizing a set of data comprising patient healthcare data for a plurality of patients over a predetermined time period;
   and contacting patients having an estimated end of life status within a predetermined threshold to offer the patient end of life care.

35. A method of incrementally updating a set of factors for input to a predictive modeling program wherein the set of factors are indicative of patient healthcare records, the method comprising:
   choosing, with a processor, a first set of factors for input into the predictive modeling program;
   receiving, with the processor, output from the predictive modeling program, such output identifying patients at risk for death in a predefined period;
   determining outcome data, with the processor, after the predefined time period has completed, which patients did die;

comparing the first set of factors with the outcome data;
determining, with the processor, which of the first set of factors achieved a greatest accuracy;
adjusting the first set of factor based on the outcome data periodically; and
recommending end of life care for a group of patients identified as being at the end of life.

36. The method of claim 35, wherein the adjustment of the factors is done annually.

37. The method of claim 35, wherein the factors comprise number of hospital stays and length of hospital stays.

38. The method of claim 35, wherein the predetermined period is used for predicting end of life within one year.

39. The method of claim 35, wherein one of the factors comprises a count of skilled nursing facility claims.

40. The method of claim 35, wherein the factors comprise one or more factors selected from the group consisting of a count of skilled nursing facility claims, a count of distinct hospital visits with congestive heart failure diagnosis, a count of distinct claims with select pain-related diagnoses, a member age as of end of year used in model, and a total amount paid for physician claims.

41. The method of claim 35, wherein the factors comprise a count of skilled nursing facility claims and at least one factor selected from the group consisting of a count of distinct hospital visits with congestive heart failure diagnosis, a count of distinct claims with select pain-related diagnoses, a member age as of end of year used in model, and a total amount paid for physician claims.

42. The method of claim 35, wherein one of the factors comprises a factor selected from the group consisting of a count of distinct durable medical equipment claims, a total amount paid for home health claims, a natural log of the payment for diagnosis related groups and a natural log of skilled nursing facility charges.

43. A system for predicting end of life for a patient within a predetermined time frame using a set of predictive models, the system comprising:
    means for storing and executing a set of predictive models on a computing device;
    means for identifying factors which have a correlation to end of life as input to the models;
    means for updating the factors based on previous successful predictions of the models;
    means for outputting a report identifying particular groups of patients meeting a certain criteria based on at least the identified factors; and
    means for recommending end of life care for a group of patients identified as being at the end of life.

44. The system of claim 43, wherein the report outputting means comprises a spreadsheet, list or other report identifying specific patients at risk for death within a specified time frame.

45. The system of claim 43, wherein the predictive models comprise configured neural net models.

46. The system of claim 43, wherein one of the factors comprises either a count of distinct durable medical equipment claims or a total amount paid for home health claims.

47. The system of claim 43, wherein one of the factors comprises either a natural log of the payment for diagnosis related groups, or a natural log of skilled nursing facility charges.

48. The system of claim 43, wherein one of the factors comprises a count of skilled nursing facility claims.

49. The system of claim 43, wherein one of the factors comprise a factor selected from the group consisting of a count of skilled nursing facility claims, a count of distinct hospital visits with congestive heart failure diagnosis, a count of distinct claims with pain-related diagnoses, a member age, and a total amount paid for physician claims.

50. The system of claim 43 wherein the factors comprise a count of skilled nursing facility claims and at least one factor selected from the group consisting of a count of distinct hospital visits with congestive heart failure diagnosis, a count of distinct claims with pain-related diagnoses, a member age, and a total amount paid for physician claims.

51. The system of claim 43, wherein one of the factors comprises a factor selected from the group consisting of a count of distinct durable medical equipment claims, a total amount paid for home health claims, a natural log of the payment for diagnosis related groups and a natural log of skilled nursing facility charges.

52. A system for predicting end of life for a patient within a predetermined time frame from the output of a set of configured predictive models, the system comprising:
    a storage component;
    a software program configured to:
        identify factors as input into the models;
        update the factors based on previous successful predictions of the models;
        output a report identifying a particular group of patients meeting a certain criteria based on at least the identified factors; and
        recommend end of life care for a group of patients identified as being at the end of life.

53. The system of claim 52, wherein one of the factors comprises a count of skilled nursing facility claims.

54. The system of claim 52, wherein one of the factors comprise a factor selected from the group consisting of a count of distinct hospital visits with congestive heart failure diagnosis, a count of distinct claims with select pain-related diagnoses, a member age as of end of year used in model, and a total amount paid for physician claims.

55. The system of claim 52, wherein the factors comprises a count of skilled nursing facility claims and at least one factor selected from the group consisting of a count of distinct hospital visits with congestive heart failure diagnosis, a count of distinct claims with select pain-related diagnoses, a member age as of end of year used in model, and a total amount paid for physician claims.

56. The system of claim 52, wherein one of the factors comprises a factor selected from the group consisting of a count of distinct durable medical equipment claims, a total amount paid for home health claims, a natural log of the payment for diagnosis related groups and a natural log of skilled nursing facility charges.

* * * * *